United States Patent [19]

Vogt et al.

[11] 4,186,112

[45] Jan. 29, 1980

[54] CATALYST FOR REDUCING CARBON MONOXIDE WITH HYDROGEN

[75] Inventors: Wilhelm Vogt, Hürth; Jürgen Koch, Brühl; Hermann Glaser, Erftstadt, all of Fed. Rep. of Germany

[73] Assignee: Hoechst Aktiengesellschaft, Fed. Rep. of Germany

[21] Appl. No.: 854,466

[22] Filed: Nov. 23, 1977

[30] Foreign Application Priority Data

Nov. 27, 1976 [DE] Fed. Rep. of Germany ....... 2653985

[51] Int. Cl.$^2$ .................. B01J 23/10; B01J 23/72; B01J 23/78; B01J 23/84
[52] U.S. Cl. .................. 252/471; 252/462; 252/472; 252/473; 252/474; 260/449 R; 260/449.6 R; 260/449.6 M
[58] Field of Search .................. 252/447, 455 R, 459, 252/466 J, 471, 472, 473, 474, 462; 260/449 R, 449.6 R, 449.6 M

[56] References Cited

U.S. PATENT DOCUMENTS

| | | | |
|---|---|---|---|
| 2,211,022 | 8/1940 | Michael et al. | 260/449.6 |
| 2,234,246 | 3/1941 | Groombridge et al. | 260/449.6 |
| 2,753,367 | 7/1956 | Rottig et al. | 252/474 X |
| 2,767,202 | 10/1956 | Rottig | 260/449.6 |

*Primary Examiner*—W. J. Shine
*Attorney, Agent, or Firm*—Connolly and Hutz

[57] ABSTRACT

Catalyst for reducing carbon monoxide by means of hydrogen so as to obtain a mixture consisting substantially of $C_1$–$C_4$-hydrocarbons. The catalyst is made by precipitating a salt of a hydrocyanic acid of the general formula $Me_I Me_{II}(CN)_x$, separating and drying the salt so precipitated and forming it. In the formula, the cationic component Me I stands for at least one of the elements Ce, Cu, Co, Ni, Fe, Mn, Zn, Ag and K or a mixture of these elements, or for Ca or Mg in admixture with $(NH_4)$; the anionic component $Me_{II}$ stands for at least one of the elements Cu, Co, Ni, Fe, Mn, Zn and Ag or a mixture of these elements; and x stands for the sum of the metal valencies; $Me_I$ and $Me_{II}$ are not permitted to stand for iron alone, or for a mixture of iron with copper.

10 Claims, No Drawings

CATALYST FOR REDUCING CARBON MONOXIDE WITH HYDROGEN

This invention relates to a catalyst for reducing carbon monoxide by means of hydrogen so as to obtain a mixture consisting substantially of $C_1$-$C_4$-hydrocarbons, the catalyst being made by subjecting a metal cyanide to partial or complete decomposition.

Ethylene is one of the most important lower hydrocarbons which are used as starting materials in the chemical industries for the commercial production of a wide variety of secondary products. In view of the considerable demand for ethylene, it is highly desirable to exploit raw material sources other than petroleum for making ethylene. One of such raw materials which recommend themselves is water gas which is obtained by reacting coal with steam at high temperatures.

The catalytic hydrogenation of carbon monoxide with the resultant formation of hydrocarbons has been described in the literature, e.g. by Winnacker-Weingaertner in "Chemische Technologie", vol. Organische Technologie I, pages 780–803, Carl Hanser Verlag, München, 1952. This reaction entails the formation of all hydrocarbons belonging to the olefin and paraffin series, which are obtained in quite different proportions depending on the particular catalyst and reaction conditions used. It has more specifically been described at page 786 of the above literature reference that in those cases in which an iron or iron/cooper-catalyst is substituted for a cobalt catalyst in the hydrogenation of carbon monoxide, olefins tend to be formed at an increasing rate while methane tends to be formed at a decreasing rate. The prior art catalysts are so-called precipitation catalyst. They are made, for example, by dissolving the metals in nitric acid and rapidly precipitating them, while hot, with an alkali metal carbonate solution. After precipitation, the precipitate is filtered off, washed out with water, dried at 110° C., crushed and screened. Next, the screened matter is reduced by contacting it with hydrogen or synthetic gas at 225° C. under a pressure of 10 atmospheres gauge.

The iron or iron/cooper-catalysts prepared in the manner just described have an unsatisfactory catalytic efficiency in the hydrogenation of carbon monoxide inasmuch as the reaction gas contains an insufficiently low proportion of $C_2$-$C_4$ hydrocarbons, especially $C_2$-hydrocarbons. In other words, the catalysts are insufficiently selective as regards the formation of low olefinic hydrocarbons.

The present invention obviates the disadvantages effects referred to hereinabove and provides catalysts which by reason of the specific method selected for their preparation enable the proportion of $C_2$-$C_4$ hydrocarbons in the reaction gas obtained on hydrogenating carbon monoxide to be considerably increased.

The present invention thus provides more specifically a catalyst for reducing carbon monoxide by means of hydrogen so as to obtain a mixture consisting substantially of $C_1$-$C_4$ hydrocarbons, said catalyst being made by precipitating a salt of a hydrocyanic acid of the general formula $Me_I Me_{II}(CN)_x$, separating and drying the salt so precipitated and forming it, formula in which the cationic component $Me_I$ stands for one or more of the elements Ce, Cu, Co, Ni, Fe, Mn, Zn, Ag and K or a mixture of these elements, or stands for Ca and Mg in admixture with ($NH_4$); the anionic component $Me_{II}$ stands for one or more of the elements Cu, Co, NI, Fe, Mn, Zn and Ag or a mixture of these elements; and x stands for the sum of the metal valencies; $Me_I$ and $Me_{II}$ being, however, not permitted to stand for iron along, or for a mixture of iron with cooper.

The forming of the catalyst (from the dried salt) is effected by (a) subjecting the salt to thermal decomposition at at temperture of 200° to 500° under vacuum or under a presure of up to 100 atmospheres absolute, or (b) subjecting the salt in contact with hydrogen or a mixture of hydrogen and carbon monoxide to a temperature of 200° to 500° C. under a pressure of 1 to 100 atmospheres absolute.

According to a further embodiment of forming the catalyst, the salt is thermally decomposed at a temperature of 290° to 350° C.

According to another embodiment of forming the catalyst, the salt in contact with hydrogen or a mixture of hydrogen and carbon monoxide is subjected to a temperature of 200° to 500° C. under a pressure of 4 to 30 atmospheres absolute.

According to still another embodiment of forming the catalyst, the salt is subject to thermal decomposition at a temperature of 200° to 500° C. under a vacuum of about 1 to less than 760 mm of mercury.

With respect to the ionic components represented by $Me_I$ and $Me_{II}$ in the general formula $Me_I Me_{II}(CN)_x$, it is advantageous for them to be used in various combinations. In those cases in which $Me_{II}$ stands for iron, $Me_I$ should preferably stand for one of the following combinations:

(a) silver, zinc, cobalt or manganese, or (b) a mixture of cooper with iron and nickel, or a mixture of cooper with cerium or cobalt or manganese, or (c) a mixture of silver with cerium or iron, or (d) a mixture of calcium or magnesium with $NH_4$.

If, however, $Me_{II}$ stands for cobalt, then $Me_I$ should more preferably stand for cooper or silver. In the above general formula $Me_I Me_{II}(CN)_x$, it is finally preferable for $Me_{II}$ to stand for manganese and for $Me_I$ to stand for copper, which is a preferred combination of metals.

With respect to the nature of the catalyst, it is possible for it to be used in the form of granules or pellets or to be deposited on a carrier, such as alumina, silicic acid, kieselguhr, asbestos, glass fibers, clay minerals, pumice or active carbon. In those cases in which the catalyst is deposited on a carrier, about 1 to 95 weight %, preferably 5 to 30 weight %, of the catalytically active ingredient should advantageously be applied to the carrier, the percentage being based on the total weight of the catalytically active ingredient and carrier.

The following statements are intended further to illustrate the catalyst of this invention.

The catalysts prepared in the manner described hereinabove can, for example, be applied to a carrier by precipitating the hydrocyanic acid salt in an aqueous suspension of the carrier, separating the resulting mixture of precipitated salt and carrier, drying the mixture, washing it and subjecting it to thermal decomposition at the necessary temperature.

Another method of applying the catalyst to the carrier comprises impregnating preformed carrier material by first impregnating the carrier with an aqueous solution of a hydrocyanic acid salt, then drying the carrier so impregnated, and reacting it with an aqueous solution of a precipitation inducting salt, or inversely.

A further preferred method comprises dry-blending the active ingredient with the carrier.

The catalyst of this invention is suitable for use in the catalytic hydrogenation of carbon monoxide by means of gaseous hydrogen to give a mixture consisting substantially of $C_1$–$C_4$ hydrocarbons. The hydrogenation can preferably be effected, e.g. by contacting the catalyst at about 150° to 500° C. and, if desired, under a pressure of up to 100 atmospheres absolute with a gas mixture containing hydrogen and carbon monoxide in a molar ratio of 3:1 to 1:2, the gas mixture being used at a rate of about 100 to 3000 normal liters (S.T.P.) per liter of catalyst per hour, and separating the $C_1$–$C_4$ hydrocarbons from the issuing gas.

It is even more preferable to contact the catalyst at 250° to 400° C. and under a pressure of 1 to 30 atmospheres absolute with a gas mixture containing $H_2$ and CO in a molar ratio of 2:1 to 1:1, the gas mixture being used at a rate of 100 to 2000 normal liters per liter of catalyst per hour.

As more fully illustrated in the following Examples, the present catalyst compares favorably with the prior art in respect of the following points: It can be made under commercially attractive conditions and combines this with a relatively high selectivity in the reaction of carbon monoxide with hydrogen to give a mixture of $C_1$–$C_4$ hydrocarbons.

EXAMPLE 1: $Ce_4Cu_{24}[Fe(CN)_6]_{15}$ 34.7 g of $Ce(NO_3)_3.6H_2O$ and 116 g of $Cu(NO_3)_2.3H_2O$ were dissolved in 1 liter of water and the whole was introduced at 60° C., with vigorous agitation, into a solution of 126.7 g of $K_4[Fe(CN)_6].3H_2O$ in 1 liter of water. The resulting precipitate was suction-filtered and washed with 1.5 liters of water in portions of 100 ml. The precipitate, which had the summary composition of $Ce_4Cu_{24}[Fe(CN)_6]$, was dried at 60° C. and the hard mass was comminuted to give particles with a size of 1.6 to 2.5 mm. 30 g of the product so made was contacted at 340° to 350° C. under a pressure of 20 atmospheres gauge with a gas mixture consisting of 50 volume % of $H_2$ and 50 volume % of CO. A constant quantity of 25 normal liters of gas was taken from the apparatus per hour. The reaction gas contained 11.25 volume % of $CH_4$, 2.45 volume % of $C_2H_4$, 1.18 volume % of $C_2H_6$, 1.7 volume % of $C_3H_6$ and 0.3 volume % of $C_3H_8$. After an operation period of 10 hours, a further 6.4 g of an unidentified oil was obtained in a separator disposed downstream of the reactor.

EXAMPLE 2: $Ce_4Cu_{12}[Fe(CN)_6]_9$

As described in Example 1, a solution of 52.05 g of $Ce(NO_3)_3.6H_2O$ and 87.0 g of $Cu(NO_3)_2 . 3H_2O$ in 1 liter of water was united with a solution of 114 g of $K_4[Fe(CN)_6].3H_2O$ in 1 liter of water. The resulting precipitate was suction-filtered, washed, dried and fragmented. 30 g of the product so obtained was contacted at 315° C. under a pressure of 30 atmospheres gauge with a gas mixture of 50 volume % of $H_2$ and 50 volume % of CO. The issuing gas was removed at a rate of 33 normal liters per hour. It contained 11.7 volume % of $CH_4$, 2.7 volume % of $C_2H_4$, 1.38 volume % of $C_2H_6$, 1.78 volume % of $C_3H_6$ and 0.52 volume % of $C_3H_8$. After an operation period of 30 hours, a further 60 g of high-boiling hydrocarbons were obtained.

EXAMPLE 3: $Cu_{1.5}Co_{0.5}[Fe(CN)_6]$

A solution of 0.75 mol of $CuSO_4$ and 0.25 mol of $Co(NO_3)_2$ in 1 liter of water was stirred into a solution of 0.4 mol of $K_4[Fe(CN)_6]$ in 1 liter of water. The resulting precipitate was suction-filtered, thoroughly washed with water and the filter cake was mixed, while moist, in a laboratory kneader with 125 g of asbestos and 125 g of fine silicic acid, the resulting mixture was dried and made into pellets 3 mm in diameter. The summary composition of the filter cake corresponded approximately to the formula $Cu_{1.5}Co_{0.5}[Fe(CN)_6]$. 40 g of pelletized material was placed in a reactor and contacted therein with gaseous hydrogen at 320° C. under a pressure of 10 atmospheres gauge. The efficiency of the catalyst so made was tested by contacting it at 300° to 310° C. under a pressure of 7 atmospheres gauge with a $CO/H_2$-mixture (1:1). A constant quantity of 25 normal liters of reaction gas was removed per hour. It contained 11.5 volume % of $CH_4$, 2.86 volume % of $C_2H_4$, 0.74 volume % of $C_2H_6$, 2.14 volume % of $C_3H_6$ and 0.31 volume % of $C_3H_8$. Under a pressure of 4 atmospheres gauge, at 290° C. and gas removal at a constant rate of 10 normal liters/h, the issuing gas was found to contain 9.38 volume % of $CH_4$, 2.0 volume % of $C_2H_4$, 0.32 volume % of $C_2H_6$, 1.37 volume % of $C_3H_6$ and 1.37 volume % of $C_3H_8$.

EXAMPLE 4: $CuFe_{\frac{3}{4}}Ni_{\frac{1}{4}}[Fe(CN)_6]$

A solution of 211.2 of g of $K_4[Fe(CN)_6]$ in 1 liter of water was admixed, with thorough agitation, with 2 l of an aqueous solution containing 137.3 g of $CuSO_4.5H_2O$, 93.2 g of $FeSO_4.7H_2O$, and 51.2 g of $NiSO_4.7H_2O$. The resulting precipitate was suction-filtered, washed with water and the filter cake, of which the summary composition corresponded to the formula $Cu_1Fe_{\frac{3}{4}}Ni_{166}[Fe(CN)_6]$ was mixed with 125 g of asbestos and 125 g of silicic acid. The mixture obtained was dried and made into pellets. 40 g of pelletized material was placed in the reactor and treated for 2 hours with $H_2$ at 320° C. under a pressure of 10 atmospheres gauge. The pelletized material was contacted at 340° C. under a pressure of 10 atmospheres gauge with a gas mixture of $H_2$ and CO, which was used in a ratio by volume of 1:1. The issuing gas was removed at a constant rate of 10 normal liters/h and found to contain: 13.6 volume % of $CH_4$, 0.81 volume % of $C_2H_4$, 2.56 volume % of $C_2H_6$, 1.61 volume % of $C_3H_6$ and 0.35 volume % of $C_3H_8$.

EXAMPLE 5: $Co_2[Fe(CN)_6]$

A solution of 1/5 mol of $K_4[Fe(CN)_6]$ in 0.8 liter of water was united with a solution of 2/5 mol of $Co(NO_3)_2$ in 0.5 liter of water. The resulting precipitate was suction-filtered, thoroughly washed with 1.5 liters of water, which contained 1/5 mol of $Co(NO_3)_2$ per liter, and then mixed with 50 g of asbestos and 50 g of silicic acid. The mixture obtained was dried and made into pellets. The pelletized material was treated at 280° C. as described in Example 4, and the resulting reaction gas was found to contain: 12.32 volume % of $CH_4$, 1.66 volume % of $C_2H_4$, 0.96 volume % of $C_2H_6$, 1.96 volume % of $C_3H_6$ and 0.35 volume % of $C_3H_8$. 36 g of higher-boiling hydrocarbons were obtained over an operation period of 55 hours.

EXAMPLE 6: $Fe_2Ni[Fe(CN)_6]_2$

As described in Example 1, a complex cyanide of the summary composition $Fe_2Ni[Fe(CN)_6]_2$ was made from $Fe(NO_3)_3.9H_2O$, $Ni(NO_3)_2.6H_2O$ and $K_4[Fe(CN)_6]$ and the complex cyanide was contacted, as described in Example 1, with a CO and $H_2$ gas mixture. The issuing reaction gas contained 32.48 volume % of $CH_4$, 0.06 volume % of $C_2H_4$, 3.44 volume % of $C_2H_6$, 1.47 volume % of $C_3H_6$ and 1.05 volume % of $C_3H_8$. A further 10 g of liquid hydrocarbons were obtained within 20 hours.

EXAMPLE 7: $Mn_3[Fe(CN)_6]_2$

As described in Example 1, an aqueous solution of 0.3 mol of $MnSO_4$ was united with an aqueous solution of 0.2 mol of $K_3[Fe(CN)_6]$ and a precipitate of the summary composition $Mn_3[Fe(CN)_6]_2$ was obtained. The precipitate was washed, dried and comminuted. 30 g of the comminuted material was contacted at 310° C. under a pressure of 4 atmospheres gauge with a CO and $H_2$ gas mixture which was used in a ratio by volume of 1:1. A constant quantity of 10 normal liters/h of gas was taken from the reactor. The gas contained 6.76 volume % of $CH_4$, 0.52 volume % of $C_2H_4$, 1.96 volume % of $C_2H_6$, 1.68 volume % of $C_3H_6$ and 0.77 volume % of $C_3H_8$.

EXAMPLE 8: $Cu_{1.5}Mn_{0.5}[Fe(CN)_6]$ 0.2 mol of $K_4[Fe(CN)_6].3H_2O$, 0.3 mol of $CuSO_4.5H_2O$ and 0.1 mol of $MnSO_4.H_2O$ were reacted in aqueous solution so as to obtain a precipitate of the summary composition $Cu_{1.5}Mn_{0.5}[Fe(CN)_6]$. The precipitate was further treated as described in Example 7. The issuing reaction gas contained 8.4 volume % of $CH_4$, 2.04 volume % of $C_2H_4$, 1.3 volume % of $C_2H_6$, 3.8 volume % of $C_3H_6$ and 0.49 volume % of $C_3H_8$. A further 25.5 g of liquid hydrocarbons were obtained during an operation period of 62 hours.

EXAMPLE 9: $Cu_{1.5}Ni_{0.5}[Fe(CN)_6]$ 40 g of the complex salt of the formula $Cu_{1.5}Ni_{0.5}[Fe(CN)_6]$ described in Example 3 was contacted at 320° C. under a pressure of 4 atmospheres gauge with a gas mixture of CO and $H_2$, which was used in a ratio by volume of 1:1. The issuing gas was removed at a constant rate of 25 normal liters/h. The reaction gas contained 17.78 volume % of $CH_4$, 0.04 volume % of $C_2H_4$, 2.2 volume % of $C_2H_6$, 0.35 volume % of $C_3H_6$ and 0.91 volume % of $C_3H_8$. Higher oily hydrocarbons could not be found to have been formed.

EXAMPLE 10: $Cu_3[Co(CN)_6]_2$ $K_3[Co(CN)_6]$ was reacted with copper acetate in aqueous solution and the resulting precipitate was made into pellets in the manner described in Example 3. 40 g of the pelletized material was contacted at 340° C. under a pressure of 10 atmospheres gauge with a gas mixture of CO and $H_2$, which was used in a ratio of 1:1. The issuing gas was removed at a constant rate of 10 l/h and found to contain 16 volume % of $CH_4$, 0.16 volume % of $C_2H_4$, 1.70 volume % of $C_2H_6$, 0.63 volume % of $C_3H_6$ and 0.32 volume % of $C_3H_8$. 2.1 g of higher liquid hydrocarbons were obtained within 13 hours.

EXAMPLE 11: $Ag_3[Co(CN)_6]$ $K_3[Co(CN)_6]$ was precipitated with $AgNO_3$ in a dilute aqueous solution of acetic acid so as to obtain a complex salt of the summary composition $Ag_3[Co(CN)_6]$. As described in Example 3, the precipitate was mixed with asbestos and silicic acid and made into pellets. 40 g of the pelletized material was contacted at 320° C. under a pressure of 10 atmospheres gauge with a gas mixture of CO and $H_2$, which was used in a ratio by volume of 1:1. The issuing gas was removed at a constant rate of 10 normal liters/h and found to contain 12.3 volume % of $CH_4$, 0.05 volume % of $C_2H_4$, 1.06 volume % of $C_2H_6$, 0.35 volume % of $C_3H_6$ and 0.49 volume % of $C_3H_8$.

EXAMPLE 12: $Cu_4[Mn(CN)_6]$ $K_4[Mn(CN)_6]$ was precipitated with the use of an ammoniacal Cu(I)salt solution to obtain a complex salt which was contacted under the conditions described in Example 11 with a gas mixture of CO and $H_2$. The issuing gas contained 1.6 volume % of $CH_4$, 0.3 volume % of $C_2H_4$, 0.4 volume % of $C_2H_6$, 0.3 volume % of $C_3H_6$ and 0.12 volume % of $C_3H_8$. Higher liquid hydrocarbons could not be found to have been formed.

EXAMPLE 13: $Mn_2[Fe(CN)_6]$

A solution of 0.2 mol of $K_4[Fe(CN)_6]$ in 1 liter of water was admixed, while stirring, with a solution of 0.4 mol of $MnSO_4$ in 1 liter of water. The resulting white precipitate, which had the summary composition $Mn_2[Fe(CN)_6]$ was suction-filtered, washed, mixed, in the manner described in Example 5, with asbestos and silicic acid and made into pellets. 50 ml of the pelletized material was contacted at 310° C. under a pressure of 4 atmospheres gauge with a gas mixture of 50 volume % of CO and 50 volume % of $H_2$. The issuing gas was removed at a rate of 10 l/h. The reaction gas contained 4.74 volume % of $CH_4$, 1.76 volume % of $C_2H_4$, 0.72 volume % of $C_2H_6$, 2.59 volume % of $C_3H_6$ and 0.24 volume % of $C_3H_8$. A further 28.3 g of liquid hydrocarbons were obtained over an operation period of 100 hours.

EXAMPLE 14: $Mg(NH_4)_2[Fe(CN)_6]$

Aqueous solutions which contained stoichiometric proportions of $MgCl_2$, ammonium chloride and potassium ferrocyanide, respectively, were united so as to produce magnesium-ammonium ferrocyanide. The complex salt was dried and 10 g thereof with a particle size of 2 mm was placed in a reactor, in which it was contacted at 320° C. under a pressure of 20 atmospheres gauge with a gas mixture of CO and $H_2$ in a ratio by volume of 1:1. The issuing gas was removed at a constant rate of 20 normal liters/h. The reaction gas contained 15.9 volume % of $CH_4$, 0.5 volume % of $C_2H_4$, 2.35 volume % of $C_2H_6$, 0.3 volume % of $C_3H_6$ and 0.77 volume % of $C_3H_8$. A further 19 g of higher liquid hydrocarbons were obtained within 22 hours.

EXAMPLE 15: $Ca(NH_4)_2[Fe(CN)_6]$

As described in Example 14, calcium-ammonium ferrocyanide was prepared and the complex salt was contacted with a $CO/H_2$-gas mixture under the conditions described in that Example. The reaction gas, which was removed at a constant rate of 20 normal liters/h, contained 11.2 volume % of $CH_4$, 1.02 volume % of $C_2H_4$, 0.85 volume % of $C_2H_6$, 0.77 volume % of $C_3H_6$ and 0.43 volume % of $C_3H_8$. A further 19.6 g of liquid hydrocarbons were obtained over an operation period of 27 hours.

EXAMPLE 16: $Zn_3[Fe(CN)_6]_2$ 0.6 mol of $ZnSO_4.7\,H_2O$ was reacted with 0.4 mol of $K_3[Fe(CN)_6]$ in aqueous solution, which contained 279 g of $SiO_2$ (Ketjen $SiO_2Fx$), so as to obtain a precipitate of the summary composition $Zn_3[Fe(CN)_6]_2 \cdot \times SiO_2$. 27 g of the mixture was contacted at 340° C. under a pressure of 9.5 atmospheres gauge with a gas mixture containing CO and $H_2$ in a ratio of 1:1. The issuing gas was removed at a rate of 15 normal liters/h. It contained 8.0 volume % of $CH_4$, 1.6 volume % of $C_2H_4$, 1.4 volume % of $C_2H_6$ and higher hydrocarbons.

EXAMPLE 17: $Ag_4[Fe(CN)_6]$

An aqueous solution of $K_4[Fe(CN)_6]$ was admixed with $AgNO_3$ so as to cause precipitation of a complex salt of the summary composition $Ag_4[Fe(CN)_6]$, which was washed with water, admixed with asbestos and silicic acid and made into pellets 3 mm in diameter. 15 g of the pelletized material was placed in a reactor and contacted therein at 340° C. under a pressure of 20 atmospheres gauge with a gas mixture containing CO and $H_2$ in a ratio by volume of 1:1. The issuing gas was removed at a rate of 10 normal liters/h and found to contain 10.71 volume % of $CH_4$, 0.7 volume % of $C_2H_4$, 1.9 volume % of $C_2H_6$, 1.71 volume % of $C_3H_6$ and 0.5 volume % of $C_3H_8$.

EXAMPLE 18: $CeAg[Fe(CN)_6]$

Cerium(III) nitrate, $AgNO_3$ and $K_4[Fe(CN)_6]$ were reacted in aqueous solution so as to obtain a precipitate of the summary composition $CeAg[Fe(CN)_6]$, which was washed and dried at 60° C. and then comminuted to fragments with a size of 1 to 2.5 mm. 30 g of the splintered fragments were contacted at 370° C. under a pressure of 10 atmospheres gauge with a gas mixture containing 33 volume % of CO and 67 volume % of $H_2$. The issuing gas was removed at a rate of 15 normal liters/h and found to contain 11.9 volume % of $CH_4$, 2.62 volume % of $C_2H_4$, 0.6 volume % of $C_2H_6$, 1.25 volume % of $C_3H_6$ and 0.25 volume % of $C_3H_8$.

EXAMPLE 19: $Ag_2Fe[Fe(CN)_6]$ 0.5 mol of a precipitate of the summary composition $Ag_2Fe[Fe(CN)_6]$ was mixed with 250 g of alumina (Condea NG) and the mixture was pelletized. 30 g of the pelletized material consisting of particles with a diameter of 1.5 to 2.5 mm was placed in a reactor and contacted therein at 320° C. under a pressure of 20 atmospheres gauge with a gas mixture consisting of 50 volume % of CO and 50 volume % of $H_2$. The reaction gas which was removed at a rate of 30 normal liters/h contained 24.1 volume % of $CH_4$, 0.99 volume % of $C_2H_4$, 4.32 volume % of $C_2H_6$, 2.04 volume % of $C_3H_6$ and 1.18 volume % of $C_3H_8$. A further 25 g of liquid higher hydrocarbons were obtained within an operation period of 26 hours.

EXAMPLE 20: $Ag_2Fe[Fe(CN)_6]$

The precipitate prepared in the manner described in Example 19 was mixed with asbestos and silicic acid and the mixture was made into pellets 3 mm in diameter. 0.5 mol of $Ag_2Fe[Fe(CN)_6]$ was blended with 125 g of asbestos and 125 g of silicic acid. 30 g of the pelletized material was contacted at 320° C. under a pressure of 20 atmospheres gauge with a gas mixture containing CO and $H_2$ in a ratio by volume of 1:1. The reaction gas, which was removed at a rate of 30 normal liters/h, contained 10.62 volume % of $CH_4$, 2.64 volume % of $C_2H_4$, 1.95 volume % of $C_2H_6$, 2.52 volume % of $C_3H_6$ and 0.67 volume % of $C_3H_8$. A further 6.8 g of higher hydrocarbons were obtained within an operation period of 18 hours.

We claim:

1. Catalyst for reducing carbon monoxide by means of hydrogen with the resultant formation of a mixture of hydrocarbons having substantially from 1 to 4 carbon atoms, said catalyst having been made by
    (A) precipitating a salt of a hydrocyanic acid of the general formula $Me_I Me_{II}(CN)_x$ in which the cationic component $Me_I$ stands for at least one of the elements selected from the group consisting of Ce, Cu, Ni, Fe, Mn, Zn, Ag and K or Ca or Mg together with $NH_4$; the anionic component $Me_{II}$ stands for at least one of the elements selected from the group consisting of Cu, Co, Ni, Fe, Mn, Zn and Ag; and X stands for a number equivalent the sum of the metal valencies; $Me_I$ and $Me_{II}$ being not permitted to stand alone for iron alone, or for a mixture of iron with copper or cobalt with copper;
    (B) separating and drying the salt so precipitated; and
    (C) forming the catalyst by
        (a) subjecting the salt to thermal decomposition at a temperature of 200° to 500° C. under vacuum or under a pressure of up to 100 atmospheres absolute or
        (b) subjecting the salt in contact with hydrogen or a mixture of hydrogen and carbon monoxide to a temperature of 200° to 500° C. and a pressure of 1 to 100 atmospheres absolute.

2. Catalyst as claimed in claim 1, the catalyst being formed under a pressure of 4 to 30 atmospheres absolute.

3. Catalyst as claimed in claim 1, wherein $Me_{II}$ stands for iron and $Me_I$ stands
    (a) for silver, zinc, cobalt or manganese, or
    (b) for a mixture of copper with iron and nickel or a mixture of copper with cerium or cobalt or manganese, or
    (c) for a mixture of silver with cerium or iron, or
    (d) for a mixture of calcium or magnesium with $NH_4$.

4. Catalyst as claimed in claim 1, wherein $Me_{II}$ stands for cobalt and $Me_I$ stands for silver.

5. Catalyst as claimed in claim 1, wherein $Me_{II}$ stands for manganese and $Me_I$ stands for copper.

6. Catalyst as claimed in claim 1, wherein the salts are thermally decomposed at a temperature of 290° to 350° C.

7. Catalyst as claimed in claim 1, wherein about 1 to 95 weight %, of the catalytically active ingredient is applied to the carrier, the percentage being based on the total weight of the catalytically active ingredient and carrier.

8. Catalyst as claimed in claim 1, wherein 5 to 30 weight % of the catalytically active ingredient is applied to the carrier, the percentage being based on the total weight of the catalytically active ingredient and carrier.

9. Catalyst as claimed in claim 1, the catalyst being formed under a vacuum of about 1 to less than 760 mm of mercury.

10. Catalyst as claimed in claim 1, wherein the separated salt in (a) or (b) under step (c) is mixed with a carrier substance selected from alumina, silicic acid, kieselguhr, asbestos, glass fibers, clay mineral, pumice or active carbon, dried and pelletized.

* * * * *